United States Patent
Etchells et al.

(10) Patent No.: US 10,575,990 B2
(45) Date of Patent: Mar. 3, 2020

(54) LIQUID DETECTING ARTICLE AND METHOD OF MAKING SAME

(71) Applicant: DRY SEE, LLC, Houston, TX (US)

(72) Inventors: Marc D. Etchells, Westhampton, MA (US); Walter G. Mayfield, Houston, TX (US)

(73) Assignee: DRY SEE, LLC., Houston, TX (US)

( * ) Notice: Subject to any disclaimer, the term of this patent is extended or adjusted under 35 U.S.C. 154(b) by 0 days.

(21) Appl. No.: 16/404,573

(22) Filed: May 6, 2019

(65) Prior Publication Data

US 2019/0336343 A1    Nov. 7, 2019

Related U.S. Application Data

(60) Provisional application No. 62/667,303, filed on May 4, 2018, provisional application No. 62/687,503, filed on Jun. 20, 2018, provisional application No. 62/783,942, filed on Dec. 21, 2018.

(51) Int. Cl.
| | |
|---|---|
| *A61B 42/10* | (2016.01) |
| *A61L 15/56* | (2006.01) |
| *A61F 13/00* | (2006.01) |
| *A61F 13/02* | (2006.01) |
| *A61F 13/04* | (2006.01) |

(52) U.S. Cl.
CPC ........ *A61F 13/00055* (2013.01); *A61B 42/10* (2016.02); *A61F 13/00059* (2013.01); *A61F 13/00063* (2013.01); *A61F 13/0206* (2013.01); *A61F 13/0223* (2013.01); *A61F 13/041* (2013.01)

(58) Field of Classification Search
CPC ........................................ G01J 3/28
See application file for complete search history.

(56) References Cited

U.S. PATENT DOCUMENTS

| | | | |
|---|---|---|---|
| 4,090,013 A | 5/1978 | Ganslaw et al. | |
| 4,285,338 A * | 8/1981 | Lemelson | A61F 13/0203 128/889 |
| 5,963,707 A | 10/1999 | Carr | |
| 2002/0040202 A1* | 4/2002 | Levin | A61F 13/0203 602/43 |
| 2003/0040691 A1* | 2/2003 | Griesbach, III | A61F 13/0273 602/45 |

(Continued)

FOREIGN PATENT DOCUMENTS

| | | |
|---|---|---|
| WO | 0061642 A1 | 10/2000 |
| WO | 2012171922 A1 | 12/2012 |

(Continued)

OTHER PUBLICATIONS

PCT/US2019/030720—International Search Report dated Jun. 27, 2019.

*Primary Examiner* — Ian A Rummel
(74) *Attorney, Agent, or Firm* — Mossman, Kumar & Tyler, PC

(57) ABSTRACT

A liquid indicating article is disclosed. It can have a single layer, but generally will have at least two layers bonded together, wherein a visible layer masks a second colored layer wherein the visible layer is a wicking material that becomes semitransparent when wet, wherein the colored layer is a permeable adhesive that bonds to the mask layer.

24 Claims, 5 Drawing Sheets

(56) References Cited

U.S. PATENT DOCUMENTS

| | | | | |
|---|---|---|---|---|
| 2007/0252115 A1* | 11/2007 | Arehart | ............ | A41D 19/0082 |
| | | | | 252/583 |
| 2009/0287130 A1* | 11/2009 | Lee | .................. | A61F 13/00021 |
| | | | | 602/44 |
| 2015/0351970 A1* | 12/2015 | Dagger | ............ | A61F 13/00055 |
| | | | | 604/361 |
| 2015/0351971 A1* | 12/2015 | Simmons | ............ | A61F 13/0243 |
| | | | | 602/43 |
| 2016/0121019 A1 | 5/2016 | Eliyahu-Gross et al. | | |

FOREIGN PATENT DOCUMENTS

| | | | |
|---|---|---|---|
| WO | 2014108682 A2 | 7/2014 | |
| WO | 2014197572 A1 | 12/2014 | |
| WO | 2018031932 A1 | 2/2018 | |

\* cited by examiner

LIQUID DETECTING ARTICLE AND METHOD OF MAKING SAME

CROSS REFERENCE TO RELATED APPLICATIONS

This application claims priority from U.S. Provisional Application Ser. No. 62/667,303, filed on May 4, 2018; and from U.S. Provisional Application Ser. No. 62/687,503, filed on Jun. 20, 2018; and from U.S. Provisional Application Ser. No. 62/783,942, filed on Dec. 21, 2018, the entire disclosure of which are incorporated herein by reference in its entirety.

TECHNICAL FIELD

The present invention relates to an article useful for detecting moisture and a method of making it. The present invention particularly relates to such an article that is compatible with medical dressings and wound covers.

BACKGROUND

Detecting moisture has long been an issue in many areas of human endeavor. For example, modern automobiles are able to detect moisture when it is in the form of rain hitting a windshield.

Another example of moisture detection would be where a catheter is used to access a patient's vascular system for treatment, such as dialysis. During that process, it is known to use an electronic sensor to detect any leakage of blood such as would occur if the catheter were removed or become dislodged.

It would be desirable in the art to be able to determine whether moisture was present in a system simply by looking at it. It would also be desirable if that could be performed without the use of an outside power supply.

SUMMARY

In one aspect, the invention is a liquid indicating article including: a first visible layer that transitions from a first opaque state to a less opaque second state, and a second layer having a color different from the less opaque state; wherein the visible layer is interlocked to the second layer and the transition of the first layer occurs while in contact with a liquid.

In another aspect, the invention is a liquid indicating article including: a first visible layer that transitions from a first opaque state to a less opaque second state, and a second layer having a color different from the less opaque state; wherein the visible layer is interlocked to the second layer and the transition of the first layer occurs while in contact with a liquid.

In still another aspect, the invention is liquid indicating article having a colored material that may include strands or particles interwoven or mixed within a wicking material that masks the colored material when dry wherein the masking material becomes less opaque when wet and exposes the colored material.

Another aspect of the invention is a liquid indicating article which is a unitary foam having: a first visible region that transitions from a first opaque state to a less opaque second state, and a second region having a color different from the less opaque state, wherein the transition of the first region occurs while in contact with a liquid.

A process for manufacturing a liquid indicating article including applying: a first visible layer that transitions from a first opaque state to a less opaque second state, to a second layer having a color different from the less opaque state; wherein the visible layer is interlocked to the second layer and the transition of the first layer occurs while in contact with a liquid.

A liquid indicating article comprising a nonwoven gauze having: a first visible region that transitions from a first opaque state to a less opaque second state, and a second region having a color different from the less opaque state, wherein the transition of the first region occurs while in contact with a liquid.

A discontinuous and permeable skin contact "gel" adhesive with gentle-release properties integrated with an absorbent foam with a wetness indicator color-change feature.

BRIEF DESCRIPTION OF THE DRAWINGS

For a detailed understanding of the present disclosure, references should be made to the following detailed description of the preferred embodiment, taken in conjunction with the accompanying drawings listed below.

DETAILED DESCRIPTION

Figure 1:
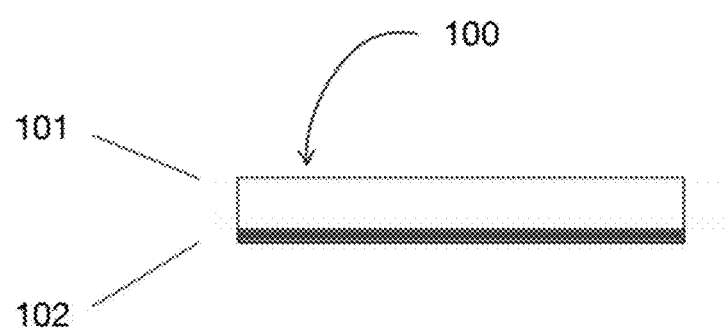
FIG. 1 is an illustration of a two-layer moisture detection article of the application.

In one embodiment, the invention is an article having at least 2 layers. The first layer is a pigmented layer. The second layer is a moisture detection layer. For the purposes of this application, the term pigmented means that the entire layer or parts thereof are of at least one color different from the second layer. Note, for the purposes of the present application, the term "color" includes both black and white as colors. The entire pigmented layer may be colored, or it may be colored in part. When colored in part the pigment may be in the form of text or graphical images. For example, in one embodiment, the word "WET" may be applied or incorporated in red against a white background. Further, the pigmented layer, in some embodiments, will allow for the passage of water through to the moisture detection layer by wicking, or any other method known to those of ordinary skill in the art.

In an alternative embodiment, the pigment can be present in the form of geometric images, a cartoon (such as a person making a 911 call), a recognizable standard image, or the like. Anything known useful to those of ordinary skill in the art to indicate that the condition of the moisture detection article has changed can be used with the invention of the application.

Similarly, any techniques known to those of ordinary skill in the art to be useful for creating mostly non translucent lettering, figures, or drawing designs that appear when the moisture indicating articles of the application becomes translucent may be employed. For example, lettering may include but not be limited to "I am wet" or some other similar phrase in any language. One technique may include molded or die cuts of woven, non woven, wicking, or non wicking pigmented or non pigmented material such as lettering that is may be placed between a first opaque or mostly opaque layer and a second pigmented layer that becomes apparent as the opaque layer becomes less opaque when wet. When the opaque layer is wetted and becomes less opaque, the die cut lettering will become visible showing for example, "I am wet." Additionally, the molded or die cut lettering may be placed on the outside visible layer if the lettering is of mostly the same color as the opaque layer and blends in until the opaque layer becomes wetted.

Continuing with this concept, the lettering, symbols, and the like may be created or incorporated into the moisture indicating articles of the application by moulding or die cutting. In an alternative embodiment, this may also be done by changing the density or thickness of the of the part of the article used to achieve the lettering, symbols, and the like. Note, nothing herein should be interpreted to mean that the indication of moisture must be of a single color because combination of colors may also be used. For example, a moisture indicating body of the application may, in one embodiment, be white when dry but then have all or part of it turn generally blue but with the term "wet" in red against the blue background.

In a different embodiment, the color of the moisture indicating material may be selected to fit with an intended use. For example, where the color indicating materials of the application are used to prepare a medical dressing then the color of the color body can be selected such that it would be substantially differentiated from red or other colored body fluids. In such applications, the color selected could be green or blue. In some embodiments, the color will be selected such that it has the greatest contrast to the masking or color indicating layer.

The pigmented layer and the moisture indicating layer may be made of any material which can be employed safely in contact or with close proximity to human skin. For example, these layers may be prepared from wood or other cellulosic pulp or chemically modified cellulose such as carboxymethyl cellulose (CMC). In another embodiment, the layers may be prepared from polymers. For example, the layers may be prepared using a polymer selected from the group consisting of polyolefins, polyurethanes, gelatins, polyacrylates, polyesters, polyolefin copolymers, polyester copolymers, Polylactic acids (CPA), collagens, polyvinyl alcohols (PVA or PVOH), silicones, and the like.

Pigments useful with the invention are, in some embodiments, those which can be used in contact with human skin. In a desirable embodiment, the pigments are either completely contained within the matrix where they are employed or are not water soluble so that they do not transfer to the patient.

In one aspect, the pigmented layer may actually serve double duty and also be a (sometimes tacky) adhesive. In another aspect, when present as an adhesive, the pigmented material may be applied as geometric shapes, as already noted above, but those geometric shapes may be such that they provide additional structural integrity to the visible layer of the moisture detecting material. In this embodiment, a pigmented adhesive may have both porosity and permeability. The fibers may be employed in geometric shapes that form trusses, arches, and other geometric shapes which provide structural integrity, especially when the materials having the fibers are wet. Exemplary of such geometric shapes are triangles, rectangles, squares, circles, ovals, parallelograms, rhombuses, and the like. In some embodiments, the geometric shapes interact to form repeating networks that further shore up the otherwise amorphous fibers. An extension of this is the use of a reactive gel or foam which becomes stiff when subjected to shear or mechanical stress. Materials with this property can be used as protection against impact or bumping. They instantly change from pliable to still upon impact. Silicone gel or foam with additives are often used in this regard.

Especially in embodiments of the liquid detecting materials of the application having two or more layers, pigmented adhesives can be employed subject to the caveat that they meet all the other properties of the pigmented layers discussed herein. Included in these properties are: allows the passage of liquids, retains its ability to adhere to the other materials of the liquid indicator when wetted with fluids including water, isopropanol, saline solution, clinical materials, and the like. For example, in some embodiments, the color adhesives may be a thermal, ultrasonic or RF laminating adhesive net, colored adhesive spray, colored adhesive strips, colored adhesive mesh, colored adhesive liquid glue, colored adhesive embedded within a masking material, and the like. Any colored adhesive that otherwise meets the criteria set forth herein for adhesives useful with the present invention may be employed within the articles of manufacture and in the methods of same.

The physical form of the materials used to make the layers may also be selected from any form known to be useful to those of ordinary skill in the art of making dressings and dressing like articles. For example, in some embodiments, either layer can be a film, expanded net or aperture film. An exemplary apertured polymeric film is 10 mil polypropylene. The film may be in the form of a net such as those sold under the DELNET® trademark or another similar colored adhesive. Additionally, in another embodiment, the colored layer may be a colored liquid adhesive that may be applied from spraying or by other conventional means. Additionally, the colored layer may be in the form of thermoplastic colored pellets, beads, grains, strips, dots, or any type of colored bonding agent of any shape solid or liquid that desirably is permeable to fluids. It may be noted that such materials are generally referred to as non-adherent surfaces, but they can also be used as a laminating adhesive and in fact are used both ways in the application for the invention.

Alternatively, either layer can be a knit, woven, flocked or nonwoven fabric. In yet another embodiment, the pigmented layer can be a foam. In another embodiment, the pigmented layer may be prepared using a gel forming material, such as a hydrogel or even just a soft foamable polymer. Still another embodiment is one where the pigmented layer is a paper or paper like material formed from wood or other cellulosic pulp.

It is important to note that the wetness indicator or masking layer may also be a foam. In some embodiments, the wetness indicator or masking layer may be fibrous. In still other layers the wetness indicator layer may be a special material such as a micro-porous or nano-porous fabric or a woven or nonwoven soluble fiber fabric like spun sugar chitosan, alginate and the like.

Where the pigmented layer is a web it can be extruded or spun. An exemplary extruded web can be 30 mil polypropylene such as that sold under the trademark NALTEX®; or supplied by Spunfab Adhesives. Low-melt thermal bonding fibers (bonding web) may also be used. In still another embodiment, the web can be prepared using reactive adhesive fibers, hot-melt adhesive fibers, and pressure sensitive adhesive fibers.

Other forms useful with the application may be selected from the group consisting of foams, hydrophilic foams, hydrofoams, superabsorbent, and the like. In one particularly desirable embodiment either layer may be a superabsorbent prepared by an aqueous solution polymerization comprising solution polymerizations of a formulation containing carboxylic acid that is cross-linked in situ when applied to the fabric upon drying by addition of a crosslinking chemical. A fiber/fabric with superabsorbent coating results. Examples of this system and suitable components to produce it are disclosed in PCT Application No. WO 00/61642 (Anderson et al) and U.S. Pat. No. 5,963,707 (Cheng et al) and U.S. Pat. No. 4,090,013 which are incorporated herein by reference. An example of the aqueous solution polymerization polymer suitable for this application is FULATEX PD-8081-H produced by H.B. Fuller Company in Vadnais Heights, Minn. Examples of suitable cross-linking agents include Bacote 20 ammonium zirconium carbonate produced by Magnezium Elektron, Inc. of Flemington, N.J. and Neocryl CX-100 aziridine crosslinking agent from Neoresins, Inc. of Wilmington, Mass.

The superabsorbent materials may be in the form of granules and/or fibers.

Turning back now to the pigmented layer, the pigment may be a part of the pigmented layer or applied to the layer. For example, in one embodiment, the pigment is applied to the pigmented layer by printing or coating the pigment onto the surface of the pigmented layer. For example, ink jet printing can be employed to do this process.

In another embodiment, thermotransfer (sublistatic) printing, roll-coating and rotogravure printing may be employed.

Rather than printing or additionally to surface pigmentation, pigment can be incorporated directly into the material of the pigmented layer. For example, where a polymer is used, color can be coextruded or co-spun when preparing fibers, in some cases by employing a color concentrate. In an alternative embodiment, the color can be added to a surface zone of the extruded or spun fiber or sheet. In still another embodiment, colored and uncolored colored fibers can be compressed or bonded to form a pigmented layer.

More than a single pigment may be employed with the articles and methods of the application.

The pigmented layer, in some embodiments, allows water to pass through it to reach the moisture detecting layer. This can be done by wicking, employing films that have microchannels, employing apertured films, or even convention film subjected to perforation, by lasers or hot needles, for example. As already stated, in a desirable embodiment, the pigments are either completely contained within the matrix in which they are employed or are insoluble in water and are thereby resistant to transferring to the patient.

The second layer can be a visual wetness indicator (sometimes referred to as a mask or masking layer herein) that is desirably a high wicking or even a super absorbent material. The second layer allows for the visual wetness indicator layer of the application becomes translucent, very translucent or even transparent when exposed to and especially when saturated with water. When dry, the composition of the visual wetness indicator is such most or even all light is reflected to an observer. The effect of contact with water is to minimize or eliminate the light reflected.

It is believed that in some embodiments of the application, for example when this layer is a fabric of fibers and the fibers are cellulosic (cotton, rayon, Tencel, etc), hydrofibers, or other fiber that can absorb water, the absorption causes the fibers to swell thereby diminishing the reflective surfaces.

In one desirable embodiment, the invention is a method of making a color body by laminating two layers together employing a method selected from the group consisting of: heat, pressure, adhesives, low-melt polymers, hook/loop (velcro), calendaring, flame lamination, fiber entanglement, felting, laser welding, rf welding, sonic welding, chemical welding, and combinations thereof. Note that such methods result in mechanical interlocking of the layers, that is the two layers engage with each other by overlapping or by the fitting together of projections and recesses. In contrast, this is different from electrostatic attraction which does not have such interlocking. Further, weak methods of bonding or joining together two layers, such as embossing, are not desirable with most embodiments of the application and are not useful as the sole source of bonding of one layer with another.

When an adhesive is used, it may be applied by spraying, dipping, wiping and any other method known to useful in applying adhesives to a substrate subject to the limitation that the bonding agent must still be able to allow for water passing through to the other layers. The adhesives useful in preparing the articles of the application include but are not limited to silicone, hot melt or acrylic adhesives.

In another embodiment, the two or more layers may be laminated by stitching. In this embodiment, stitching is used to hold the layers of the article together.

One application for which the articles of the application are particularly suitable is dressings and bandages. For example, a common bandage can be prepared with an article of the application sandwiched between the surface contacting a wound and a water and occlusive dirt proof transparent outer layer. When dry, the bandage would appear normal. Should sufficient moisture, either from the wound itself or as contamination seeping into the side the bandage, penetrate the bandage to render the opaque layer transparent, then the color of the first layer or a illustration thereon would become visible indicating that the integrity of the bandage to moisture has been breached.

One advantage of the articles of the present application is that they can be reused in some embodiments. The third layer of the article may regain opacity when dried, thus the liquid indicator process is reversible.

In some embodiments it may be desirable to employ an additional layer of wicking material that is more aesthetically pleasing material adjacent to the first layer. This would be particularly useful when the subject layer would be against skin. Similarly, an additional layer which is configured to prevent the dressing sticking to a wound may be so employed.

In one embodiment, the article of the application may include an additional layer that is adjacent to the moisture indicating layer that is a transparent film coated with an adhesive. This embodiment, which would include bandages, could be prepared in fixed sizes, or it could be prepared and sold in the form of rolls.

In one particularly desirable embodiment, a roll of the article of the application could be used to monitor the integrity of a plastic bag or other form of water exclusion device for use with a limb having a cast or open wound. A process of the application can be performed by first taking a roll of the article of the application and adhering a continuous strip above the cast or wound. Next, a plastic bag could then be placed over the limb to a point above the article of the application and then sealed against water. The person using this method within be able to take a bath or shower and then monitor the article of the application to ensure that no water had penetrated the water exclusion device.

In embodiments where the article of the application is in the form of a roll, the article may employ a tacky adhesive, either with or without a removable protector strip, applied to the surface of the moisture indicating layer. Also useful with such embodiments, would be a dispenser, especially one which would be useful for cutting the article to desired lengths. In an alternative embodiment, the article may be perforated at selected intervals to allow for the dispensing of standard sizes.

The articles of the application may be employed in many different end-uses. For example, they may be used to protect scars from sunlight. They may also be employed in dressings having antibiotic properties. In another embodiment, the most or all of the components of the article of the application are elastic allowing for the use of such an article in a dressing that serves to put traction on wound to aid in prevention bleeding or scarring.

The articles of the application may also have other components incorporated therein. For example, in one embodiment, the article of the application may have an additional layer of an expanded foam to allow for longer term wicking of fluids.

In some embodiments of the invention of the application, the moisture detection body is a two-sided lamination with a wetness indicator layer in the center of two materials. In other embodiment, the moisture detecting body is a one-sided lamination with wetness indicator layer on one side of an absorbent or wicking material.

The pigmented layer can be an apertured netting (Delstar) or fibrous web or printed pattern. This may be used with a color indicating layer that is prepared utilizing cotton fibers up to the 100% level in an absorbent layer.

In one desirable application of the color detecting bodies of the application, one or more layers may include a medicine delivery system. For example, in one embodiment, the color detecting layer may include a him a static agent and/or a silver-ion releasing antimicrobial system. Antimicrobials which function more rapidly than silver may be used and include quaternary ammonium compounds and oxidizers such as iodine, chlorine or chlorhexidine gluconate (CHG).

In another embodiment, rather than medicine per ser, other compounds can be delivered to skin or a wound. For example, humectants are added to the mix to attract moisture from the atmosphere to partially hydrolyze and soften the fiber/fabric absorbent treatment. Suitable humectants include glycerin (glycerol), propylene glycol (PEG), ethylene glycol, mineral oil, lanolin, sorbitol, maltitol, and sodium PCA. Glycerin is a preferred humectant and can be purchased from Cognis Corp., Cincinnati Ohio. Polyethylene glycol is also preferred and can be purchased from Dow Chemical, Houston, Tex. under the trade name of Carbowax. Honey can also be used as an antibiotic or probiotic.

The Wetness indicators of the application may be those utilizing adhesive for self-adherent features.

Where the pigmented layer is in contact with a wound or other skin section, it may be desirable to utilize a non-adherent netting (such as those provided under the DELNET trade designation) on an outer surface for direct wound contact. Alternatively, a pigmented layer with a low heat melt on each side such as a fibrous colored netting clad between heat applied melted strands may be employed. An apertured or perforated film is an alternative, including laser perforations on a thin breathable PU or non-breathable PE film.

The moisture indicator of the application is especially useful in the following applications: shower protective device; wound care dressing such as like Molnlycke Mepilex and the like; absorbent gauze (like Kendall Kerlix 4×4); and tube/port entry protective device and (such as J&J BioPatch), or a thin film occlusive dressing (like 3M Tegaderm).

Variable moisture indication can be performed by employing moisture indicating bodies of the application preparing using more than one pigmented layer. For example, in one embodiment, the pigment of the first layer can be of a color or color intensity that is comparatively easy to see through the color indicating layer. Different colors or color intensity can then be employed that are only visible when the color detecting layer is fully saturated.

When a separate masking layer is present in the application, it will have a desirable weighting of from about 25 to about 160 $g/m^2$. In some embodiments, this range can be from about 40 to about 125 $g/m^2$ and in still others from about 50 to about 100 $g/m^2$. The masking and pigmented layers of the application desirably retain most if not all of their structural integrity and bonding when wet. Such layers also are highly wicking or otherwise facilitate the transport of water. It is important to note that if the weight and/or thickness is too high then the transparency through a mask is inhibited even when wet and is to be avoided. Similarly, if the weighting is too low, then the contrast is insufficient to send an unmistakable wet and dry indication.

While, generally, the moisture detecting articles of the application will have at least two layers, in some embodiments they may have only a single layer combining the properties of the two separate layers described above. Foams structures can be employed in such embodiments.

In such applications, one embodiment would be a foam structure in which the foam is co-extruded or cast with a pigmented side or layer and a moisture indicating side or layer. In an alternative embodiment, a pigmented foam may be bonded by chemical or thermal, ultrasonic or RF lamination of the foam to a non-woven mask, especially one that turns more translucent when wet. In yet another alternative design, the moisture detecting material is a foam to which one side has been treated with a pigment via a printing, casting, coating, spray, or similar application technique. For example, Dow Hypol 2002, a hydrophilic prepolymer, can be cast to a desired thickness and then surface coated on one side with the pigment. In the alternative, a fibrous textile fabric in which fibers are woven, knit or placed in distinct zones, layers or structures can be employed. Some fibers will contain the pigment and others will act as the moisture indicator. As the density increaser or the viscosity decreases, a foam becomes more gel-like. A gel/foam structure is an alternative in this application.

Another example of such an embodiment is one where a warp or circular knit structure in which all the fibers, filaments or yarns on one surface are chosen to create the moisture indicating effect and the alternate side is composed of fibers, filaments or yarns which are pigmented. The color may achieved in a traditional textile dyeing or printing operation or a specialized application of a metal, preferably silver, for antimicrobial properties. An example is the Silverlon™ dressing (https://www.silverlon.com). The liquid indicating articles of the present application may be employed in medical dressings. For example, in one desirable embodiment, the liquid indicating articles of the present application are employed in a dressing such as those disclosed in WO 2014/197572 which application is incorporated herein in its entirety. In one particularly desirable embodiment, such a dressing is prepared employing the liquid indicating article of the present application around the periphery of the dressing. In yet another embodiment, the colored indicating material is also employed over the center of the dressing so that it may be employed with wounds that need to be monitored for both liquid infiltration and saturation due to bleeding or exudation. In still another desirable embodiment, the center part of the dressing can include additional padding capable of passing moisture to be used with shingles, a condition that is often hyper sensitive to touch but also having blisters which can exude prodigious amounts of fluid.

The invention of the Application also includes those embodiments where the they are incorporated into a dressing shaped like a glove or sock. In these or any dressing end-use applications, the material of the dressing may be sufficiently inelastic as to be able to apply pressure to keep an incision or wound closed to prevent bleeding and/or promote healing.

In still another embodiment, the invention is an absorbent antimicrobial color liquid indicator that can act as a wrist band. The wrist band may be used by doctors and health care providers to help determine medical glove wetness saturation and help prevent microbial laden fluids from escaping from the tops of surgical gloves and to determine when too much fluid has been built up in a glove. In a similar embodiment, the glove can be a surgical glove. In still another similar embodiment, the band can be applied to a pic line to indicate fluid migration. In some embodiments, the band is wrapped around a pic line.

Another embodiment of the invention is a hospital incontinence pad. In such a pad, a liquid indicating article would be incorporated therein such that hospital workers could quickly remove saturated pads. These would be particularly useful with patients who are unconscious or otherwise able to indicate a need for changing pads to an attendant. In the pads of the application, the color indicating material is placed in the pad at a point to indicate that the pad is saturated but only at the periphery of the pad to prevent the color indication material from interfering with the pad's ability to keep the patient's skin from becoming overexposed to moisture and susceptible to skin maceration.

Referring back to embodiments of the invention where the moisture detecting articles are in the form of a foam, the foams may be rectangular, but in a desirable embodiment, the foams will be tapered. When in a tapered form, the foam will have less propensity to have a gap form between the edge of the foam and the adhesive layer of a dressing. This can be particularly desirable in applications where the wound produces a lot of liquid. By minimizing the gap, there is less likelihood that the dressing will pull away from the skin of a patient wearing it thereby destabilizing the dressing.

In embodiments where the moisture detecting articles are a foam taper, they may be contoured in a curve inward or outward. The taper may have a continuous curve for some or all of the foam taper. The foam may be tapered on one or, oin some embodiment, on both sides of the foam. The purpose of the contoured foam may include limiting the edges from swelling that may lift the bandage exterior off the skin.

In some embodiments of the invention, the moisture detecting articles will be adhesives. Generally speaking, when an adhesive, the moisture detecting articles are tacky adhesives. This is, of course, not to be confused with situations where an adhesive is applied to an article of the present application.

The moisture detecting articles of the application may comprise antimicrobial additives. The antimicrobial additives may be employed either by incorporating them during the production of the moisture detecting articles or by applying them to the moisture detecting articles.

In addition to antimicrobials, another clinical material useful with the moisture detecting articles of the present application is a hemostatic dressing. Such a dressing would consist of a breathable occlusive layer having a moisture detecting material of the present application applied to the exterior surface. The pigment used would be chosen such that it would complement the deep red oven active arterial bleed are other type of suit burial bleed so that there would be a sufficient color change visible to a care provider. Any hemostatic agent known to be useful to those of ordinary skill in the art can be used with the present application. Exemplary materials for this in use include but are not limited to oxidized cellulose, non-oxidized cellulose, clay, zeolite, polymers having ionic groups, and the like. One particularly desirable hemostatic composition useful with the present invention is that disclosed in US Patent Application No. 20160121019 which is incorporated herein by reference in its entirety.

Referring to hemostatic compositions, cotton fibers offer varying degrees of blood clotting performance. In contrast, synthetic fibers offer almost zero performance. In at least one embodiment of the invention, clean but unbleached cotton is employed, with or without some synthetic fibers, to increase the blood clotting properties of dressings prepared using the materials of the application. The advantage of using unbleached cotton is believed to be the residual pectin.

Another hemostatic embodiment of the application is a composition of cotton fibers, preferably unbleached, treated with kaolin and clay, zeolites, chitosan, and the like, to further increase clotting performance.

In still another embodiment, a dressing prepared with materials of the application will have improved hemostatic performance by employing cotton fibers that have been modified to be gel forming and/or re-absorbable.

In some embodiments, it may be desirable to incorporate antimicrobial properties into the materials of the application. While this may be done in any way known to be useful to those of ordinary skill in the art, it may be particularly desirable to employee silver ions. The composition sold under the trade designation SILVADUR by the DuPont® company may be particularly desirable. When employing silver ions, it is particularly desirable to employ them within a foam, on a foam as a coating, and on a gauze as a coating.

When employed in dressings, the tapered foam materials of the application need not be pigmented nor liquid indicating to impart desirable qualities to the dressing. A foam dressing that is tapered from the edge at less than 30° for more than one quarter of its width or length has properties that help prevent outside adhesive layers from lifting off skin due to the exterior swelling of the foam went saturated with a liquid. A thin outer edge of the tapered foam with a thickness between zero and 2 mm thick may be desirable to minimize outer edge swelling when wet. Additionally, the foam may be continually tapered across its body in all lateral directions.

Another embodiment of the invention of the application is a dressing having two or more section of moisture detection. Such a dressing is configured not only to indicate that the dressing is becoming saturated, but also to indicate whether the saturation is coming from the wound being covered are from outside of the dressing. In this embodiment, when employed by a patient having a wound, if the liquid indicating article closest to the wound changes color first, then it can be reasonably assumed that the liquid is coming from the wound. In the alternative, if the liquid indicating article furthest from the wound changes color first then it can be assumed that the liquid is coming from outside of the dressing. Three, four, or even five or more applications of the moisture detecting material can be employed in such a dressing.

In order to assist someone not familiar with a article of manufacture employing a moisture detection composition of the application, dressings are other end-use applications prepared using the moisture detection compositions can be configured such that part of the pigmented part of the moisture detection material is visible even when the material itself is dry. Such a configuration can be prepared in any way known to be useful to those of ordinary skill in the art. In one such embodiment part of the masking layer can be paired away. Our in the alternative, the pigment pigmented material can be slightly larger than the masking material and folded over so it's visible even when the moisture detecting material is in use and dry.

In yet another embodiment, articles prepared using the moisture detecting materials of the application may have part or all of the external part of that article be of the same color and or intensity of the pigmented material. One unfamiliar with the use of the article could then use the exterior of the article as a guide to knowing when the moisture detecting material has change colors. In this or any other embodiment of the compositions of the application, where the moisture detecting materials of the application are employed in another article, then the article should be translucent and preferably transparent over the moisture detecting material to allow one using it to observe any color changes that may occur.

In some embodiments, the moisture indicating materials of the present application undergo a color change in the presence of a very small amount of moisture. While some slight absorption is of course inherent, desirably the materials of the present application will require only de minimis amounts. This can be important. For example, when employed with a dressing, if the liquid indicating article absorbs a large quantity of fluid, it makes changing the dressing quite problematic. In the process of changing the dressing one could easily squeeze contaminated fluids out of the dressing back into a wound for example.

In one embodiment, the liquid indicating articles of the present application undergo a substantial color change when contacted liquid having a weight equivalent to 30% of the non-pigmented part of the liquid indicator material. In another embodiment, the amount of liquid needed is 15%. In still another embodiment, the color change occurs with 10%.

Referring now to the substantial color change, for the purposes of the present application, this term is defined to mean a color or appearance change sufficient to be obvious to a human or instrumental observer. In some embodiments, this change could be of a magnitude of at least 10% of the dry L (lightness) or C (chromo) values of the article when tested as below in Example 2. In other embodiments, the change may at least 20%. And in still other embodiments, the change may be as much as 30%.

The moisture detecting articles of the disclosure change color when coming into contact with liquids, especially water. This is important because water, infiltrating a dressing, is essentially invisible. When employed in applications such as a dressing to detect water intruding into the dressing, a sharp contrast between the moisture detecting article in the dry state and the moisture detecting article in the wet state is important.

The moisture detecting materials of the application, in contrast to the materials of the prior art, retain substantial integrity when wet. In many end-use applications, having a moisture detection material comprising substances such as paper is undesirable because such substances lose their structural integrity when wet. Unless those materials are encapsulated or in some way prevented from disintegrating, they can cause problems. For example, in a dressing, such materials could compromise a wound. In other applications they could cause or give rise to undesirable aesthetics.

It follows then that it would be desirable that moisture detecting materials would retain their structural integrity when wet. For purposes application, unless otherwise indicated, the term wet means wet as in wet with water. That being said though, it is also desirable that the compositions of the application retain their integrity in the presence of liquid such as isopropyl alcohol, sailing, common clinical materials, and the like.

The moisture detecting materials of the application may be prepared using any manufacturing process known to be useful to those of ordinary skill in the art. For example, when combining or applying natural fiber nonwovens to polymer or copolymer materials, the individual components can be heat molded together. Similarly, they can be glued together.

When the moisture detecting materials of the present application are a foam, in one embodiment the foam is shaped into a tapered structure instead of a rectangular This is accomplished via using a shaped 3-dimensional mold into which the breathable occlusive layer and color change layers are inserted and formed into the shape of the mold. This can be accomplished using any molding method known to be useful to those of our nurse on the heart. For example, the molding can be done via vacuum molding, heat molding, extrusion molding, and in some applications, even reaction injection molding. A sheet of cast foam can be compression molded as it cures and develop strength.

Whatever the molding method, the components are mixed and introduced onto a breathable occlusive layer and color change layers. The foam is selected such that it does not require excessive heat in drying or generate excessive moisture which must be removed. By eliminating the excessive moisture or high heat, this foam can be cast and cured directly in the shaped 3D mold. The benefits of such a material are as already discussed above, but especially advantageous for producing more secure dressings that do not become destabilized as they absorb fluids.

In one embodiment, a foam type liquid indicator of the application would comprise a breathable occlusive layer which is a laminate of 1) any film (olefin, urethane, polyester, or thin fibrous nonwoven or paper which offers the properties of breathability (moisture vapor transmission over 400 g/m2/24-hrs), strength, softness (drape) and low coefficient of friction; and 2) any material which exhibits a color shift when wet and functions as the as the indicator.

For this embodiment, it could be desirable to employ a silicone, gel, are solvent acrylic adhesive.

When the adhesive used to prepare the liquid indicating articles of the application is a polymer netting, then it is especially good at incorporating additional dimensional stability to the moisture indicating materials. The netting provides stability in both the X and Y directions, acting somewhat like rebar and concrete.

In addition to providing stability, that is improving the ability of a dressing to continue to adhere to skin in the presence of moisture, by employing a tapered foam having a comparatively thick center and very thin extremity, the material could be employed to deliver those components discussed elsewhere.

In one embodiment the foam liquid indicator of the present application may comprise a pigmented foam with a mask that turns translucent or transparent when wet. In another similar embodiment, the foam may have a pigmented region and a masking region that turns transparent or translucent when wet in place of a separate mask.

The foam element of all moisture detecting materials is desirably as thin as possible, subject to having a sufficient thickness to effectively block the view of a user to the pigmented material (whether provided as part of the moisture detecting material are in situ by a wound) when in a dry state.

Such foams are prepared using technology well known to those of ordinary experience in the art of preparing polymer foams. Most such foams are prepared using toluene diisocyanate and methylene diisocyanate for an A side. The B side components are typically polyols, especially polyethylene glycol base polyols. The use of pre-polymers is common in this art area also. In some embodiments, hydrogel type polymers are the most preferred. Hydrogel polymers are known in the art, and are disclosed in U.S. Pat. No. 6,080,488, which is incorporated herein by reference in its entirety.

Many wound care materials have a non-adherent layer against a wound to prevent adhesion (such as Delnet). Most bandages are adhesively applied to the patient and a preferred adhesive is a low-trauma type. These adhesives are often referred to as "gel" silicones or hybrids which mimic a "gel" silicone. Dow (now Dow DuPont) is a leader in the field with their brand of SoftSkin Adhesives. SoftSkin is an example of adhesives and hybrids that can function as both an adhesive and a wound non-adherent layer; they can be placed directly on an open wound to provide attachment and then removed with minimal pain. It is important, however, to provide voids in the adhesive layer for fluids and gasses to pass and these "gel". Imparting these voids is challenging as conventional perforation techniques do not perform well with gels; the layer of gel effectively closes a hole and heals itself. An important variation has been discovered which effectively allows the placement of a discontinuous "gel" low-trauma adhesive on the surface of an absorbent foam with the optional use of a liquid indicator feature all in one continuous manufacturing process. Shaped or products can be produced as well as continuous rolls.

The moisture detecting materials of the application can be employed in a great number of end-use applications. For example, in addition to the already referenced dressings, they could be useful in lab and hospital where. Exemplary of such things are: hospital gowns, masks, booties, and the like. In embodiments where the moisture detecting materials of the application have properties similar to that of gauze, then it would be desirable to employee where saturation with moisture could be an issue, especially when that moisture our liquids is something not easy to visually detect such as lymph. One such end-use in this category would be packing around a transcutaneous device our appliance such as a surgical drain tube. One advantage of the materials of the application are that they can not only indicate when something is becoming saturated but can also indicate when something is drying out. There are numerous medical issues were that could be important.

The materials of the application may be prepared using any method known to be useful to those skilled in the art of preparing such materials. However, in one embodiment, a material of the application is prepared by depositing an adhesive on a carrier or release liner (layer 1). This adhesive (layer 2) may be continuous, discontinuous, or even in sections or patterns.

The preferred adhesive for this embodiment is a silicone "gel" which attaches well to patient's skin but also releases with minimal pain or trauma. Dow Corning 9700 to 9010 family of silicone Soft Skin adhesives are typical for this application and are in fact used in this example. Several versions of a low-trauma non-silicone adhesive are also suitable. Often referred to as Hybrid adhesives in the art of preparing the dressings. Additionally, Hot Melt, Hydrocolloid, Polyurethane and Acrylic adhesives are some of the many other options which could be used in place of the silicone gels. It is to be noted that Acrylics and Urethanes are generally a 2-part system requiring highly controlled meter mixing head up application.

Application of the adhesive may be via a computer-controlled 3D printer or X-Y motion with one or more nozzles. Rotogravure or any other deposition technique known to be useful to those in ordinary skill in the art may also be employed. The pattern and quantity (thickness) of adhesive may be non-uniform and open areas allowing fluid/air movement may be desirable.

The adhesive may be natural or pigmented with a non-leaching pigment such as a dark blue. If a pigmented adhesive is used, more than one color are possible. The use of patterns, words, and symbols it is also possible.

Gentle heat may be applied to overcome the silicone crosslinking inhibitor and initiate the crosslinking reaction. This step may also be omitted until later. It is important to realize that not all adhesives require this heating step.

On top of the release liner and deposited adhesive is cast a hydrophilic foam layer (layer 3). This layer can be up to 10 mm thick, but 2-4 mm is typical for wound bandages. Thick/thin sections may be created which may also include a tapered perimeter.

The foam may be applied from a roll if it was produced in a prior step or sourced from a vendor. A preferred method of manufacture is a direct application of components which are mixed and react to generate gas bubbles and create a foam. Multi components are mixed thoroughly, generally, a polyol Part A with an aqueous/surfactant as Part B. A hydrophilic foam results and because it was cast onto the adhesive, it is firmly attached while not inhibiting the adhesive from functioning.

Multiple layers of foam are possible. Absorption capacities, softness, color, thickness, additive additions and many other variables are possible. For example, a low-cost roll or commodity foam may be married to a high-performance urethane hydrophilic foam to reduce costs. Superabsorbent granules or antimicrobials may be placed in different layers to impart special features.

Several Polyurethane Prepolymer chemistries are available and useful in foam production. HYPOL family from Dow, AQUAPOL by Carpenter and BAYMEDIX by Covestro are all candidates. Mixing ratios and processing/drying conditions vary. Each can be modified by adjusting the mix to control capacity, density, strength, etc. Additives and colors can be mixed prior to, or at, the final mixing head.

Most dressings utilize an occlusive breathable film outer layer to prevent outside contamination from bacteria while allowing airflow for wound health. Polyurethanes, Polyesters and hybrid films with a thickness of 0.0005" to 0.002"

are typical. This occlusive layer (layer 4) may be deposited on top of the foam layer (layer 3) while in production. A strong intimate bond results.

By following this general process, complex dressings with adhesive, absorbent foam and occlusive barrier film may be produced in one process. If a pigmented adhesive or pigmented foam layer is utilized, a wetness indicating structure results. This structure may be modified in numerous ways to produce advanced and high-performance wound dressings economically.

The materials of the application may be employed in end uses that require the materials to be exposed to moisture. The bonding between the layers of the materials of the application are water resistant. Further, the water indicating materials of the application, when exposed to moisture, retain sufficient structural integrity that they do not fall apart. In some embodiments, the moisture indicating materials of the application retain most of their structural integrity after being exposed to moisture. For purposes of this application, the term water resistant means that an article that is moisture resistant retain sufficient structural integrity that it does not fall apart when wet.

The moisture indicating materials of the application are able to maintain their structural integrity, or at least most of it, when wet with both aqueous and liquids typical of a medical environment, such as isopropanol. The articles of the application will have tensile properties such that an article composed of: nonwoven cotton/film, expanded net or aperture film/nonwoven cotton; of at least 150 to at least 400 g/in (grams per inch) for dry materials. For saturated articles that have been soaked in water (with or without saline) for 24 hours, at least 125 to at least 350 g/inch. And for saturated articles that have been soaked for 24 hours in isopropanol at least 75 to at least 250 g/inch.

Similarly peel strength ranges for such articles would be at least 75 to at least 200 g/inch dry. For saturated articles that have been soaked in water (with or without saline) for 24 hours, at least 30 to at least 175 g/inch. And for saturated articles that have been soaked for 24 hours in isopropanol at least 25 to at least 150 g/inch.

Tensile and peel strength testing can be performed by any method know to those to be useful in the including, but not limited to ISO 9073-3.

The moisture indicating materials of the application can be employed using materials other than or in addition to known clinical materials. For example, in one embodiment the moisture indicating materials of the application are employed to treat a wound using probiotic products. Homeopathic materials may also be employed to treat not just wounds but also other skin conditions. For example, a great deal of work is being done using *cannabis* oil, commonly referred to in the art as CBD oil, to determine what health benefits can be achieved using this material. One end-use of the materials of this application would be to use them to either treat a skin condition, a wound, are as a mechanism for transdermal introduction of the oils to the human body. The moisture indicating materials of the present application would be particularly useful with such applications where liquid intrusion from either the outside or the interior of the body would compromise such treatment.

The agents, additives, medicines, moisturizers, and the like may be introduced into the articles of the application in any way known to be useful. For example, when the moisture indicating article of the application is or includes a foam, the material could be introduced into the foam formulation as it is mixed for extrusion, injections, and the like.

In some embodiments, the liquid indicating articles of the application may be a unitary foam or nonwoven gauze. In these embodiments, the unitary articles function like a two-layer article where the transitioning region masks a pigmented region until it comes into contact with a liquid. For a unitary foam, the two regions can be coextruded or applied one upon the other. For a nonwoven unitary article, the two regions can be formed by knitting with a pigmented yarn being used in conjunction with a transitioning yarn.

In still another embodiment, the a liquid indicating article of the application is prepared by making a matrix that is opaque when dry and transparent to translucent when wet and introducing into the matrix, either after or at the time of producing the matrix, a pigment such that the pigment is masked in at least one direction by the unpigmented matrix. These matrixes are especially useful in making dressings. A preferred adhesive in a medical bandage is one which adhere well to the skin yet is easy to remove without pain. Such an adhesive, when placed in direct hair-contact releases without pulling the hair. Silicone gel adhesives are often used with good performance at a 0.006" to 0.008" thickness for such applications. A newly developed acrylic adhesive which utilizes a catalyst for internal crosslinking also offers good performance but at a 0.002 to 0.004" thickness while also offering a cost reduction.

While the liquid indicating article of the application do indicate the presence of liquids, embodiments of same wherein no pigment is used is within the scope of this disclosure. For example, a thin tapered foam of the application could be employed in application wherein the presence of liquid is not relevant, but would instead contribute to the stability of a dressing and prevention of the exterior adhesive from being lifted up from skin.

In one embodiment, the pigment used to prepare the liquid indicating article of the application is also an additive such as an antibiotic or a hemostatic material. When applied to a "wet" wound (that is a wound that is actively bleeding or weeping lymph or plasma, such as a burn), in addition to indicating that the presence of a liquid, the liquid indicating article of the application would also deliver the additive to wound.

As has been stated above, the liquid detecting articles of the application may be prepared using any method known to those of ordinary skill in the art, but may also be prepared using advanced methodology. For example, in one embodiment, a foam of the application is prepared employing nano-bubbles. In still another embodiment, employing nano-emulsions.

While the use of paper, which can disassociate into very fine fibers, is not within the scope of this application for use as a masking layer, the use of dissolvable film is within the scope of the application. In this embodiment, a dissolvable film is prepared using components that safe for the application for which they would be employed. For example, in one embodiment, a first layer of polyvinyl alcohol film is employed to mask a second layer which is a pigmented apertured (an non-dissolving) film or net. When liquid contacts the first layer, it dissolves or at least becomes translucent. This is an exception as most or all of the materials used to prepare the articles of the application are liquid resistant. These dissolvable films are distinguishable over other dissolvable materials because those materials, such as dissolvable paper, can be undesirable since they do not truly dissolve but rather disassociate into fibers which can be undesirable in may end-use applications. In addition to the matter already claimed, other subject matter that may be the subject of claims includes, but is not limited to embodiments: where the visible layer and the colored layer are adhesively secured to a foam; where the visible layer is a foam that is thermally bonded to a pigmented foam; where the foam is tapered and/or tapered to angle of less than 30 degrees; the article is a unitary foam having: a first visible region that transitions from a first opaque state to a less opaque second state, and a second region having a color different from the less opaque state, wherein the transition of the first region occurs while in contact with a liquid; and the article is a nonwoven gauze having: a first visible region that transitions from a first opaque state to a less opaque second state, and a second region having a color different from the less opaque state, wherein the transition of the first region occurs while in contact with a liquid.

DISCUSSION OF THE DRAWINGS

Turning now to FIG. 1, a moisture indicating article is shown (100) where a moisture indicating layer is shown (101) bonded to a pigmented layer (102). When in use, the moisture indicating layer is opaque when dry and translucent or transparent when wet. When in use, the pigmented layer is masked from an observer until the moisture indicating layer becomes wet.

Figure 2:
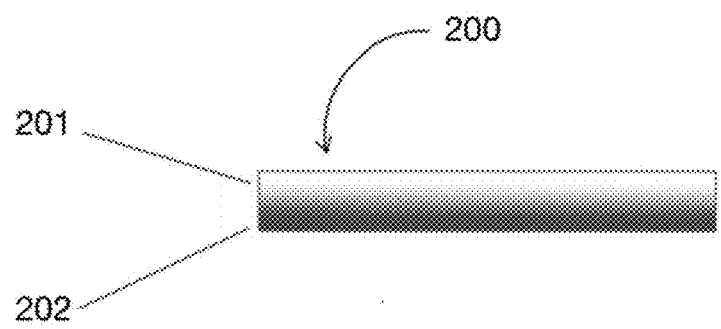
FIG. 2 is an illustration of a single-layer moisture detection article of the application.

Turning now to FIG. 2, a moisture indicating article is shown (200) where the article is a single layer. This article has a moisture indicating zone (201) and a pigmented zone (202). When in use, the moisture indicating zone is opaque when dry and translucent or transparent when wet. When in use, the pigmented zone is masked from an observer until the moisture indicating layer becomes wet.

Figure 3:
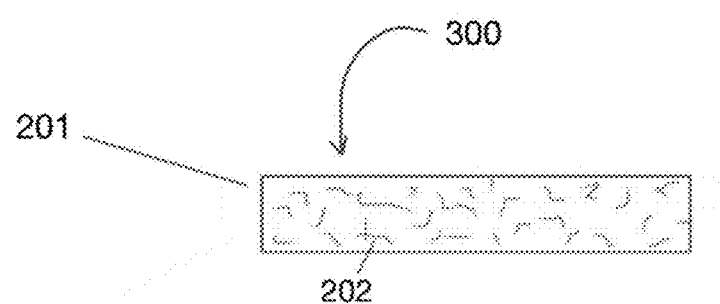
FIG. 3 is an illustration of single-layer moisture detection article of the application where the article is prepared using bonded fibers.

Turning now to FIG. 3, a moisture indicating article is shown (300) where the article is a single layer of bonded fibers, most of which are unpigmented (301). There are also much a smaller number of pigmented fibers (302). When in use, the pigmented fibers are not visible because there are too few at the surface of the article to be seen. When the article becomes wet and translucent, then the fibers that were masked from an observer are visible in a quantity sufficient to be perceived.

Figure 4:
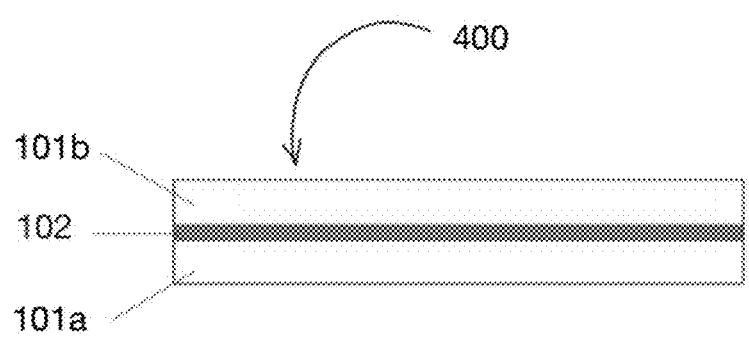
FIG. 4 is an illustration of a three-layer reversible moisture detection article of the application.

Turning now to FIG. 4, a moisture indicating article is shown (400) where the article is a three layer, reversible, moisture indicating article, that is it can be used to indicate water movement from any direction. The article includes a single pigmented layer (102) and adherent thereto two moisture indicting layers (101a) and (101b).

Figure 5:
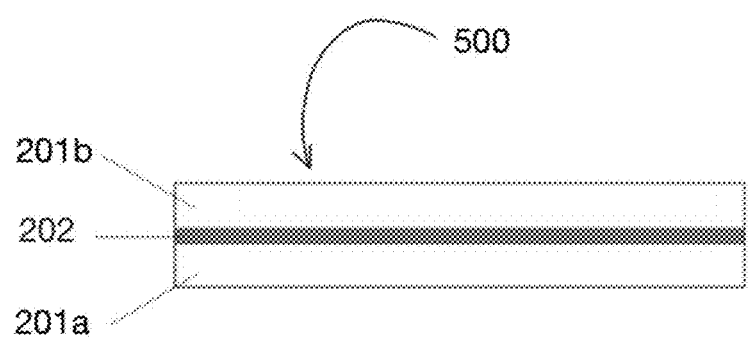
FIG. 5 is an illustration of a single-layer reversible moisture detection article of the application.

Turning to FIG. 5, a single-layer, reversible, moisture indicating article (500) is shown. In this embodiment, a foam or fibrous matrix having a central zone which is pigmented (202) and two zones on either side which are unpigmented is shown (201a) and (201b). The matrix is opaque when dry and transparent to translucent when wet.

The water indicating materials of the application can be prepared using any conventional process known to be useful in the art for making such items. In one embodiment, a two-layer material is made by applying to a white or non-colored mask, a woven or non-woven colored adhesive. In another embodiment, a first mask material having a first melting point is subjected to a spray or calendaring application of a second material having a second melting point sufficiently lower than the first melting point such that the two materials adhere to one another.

The two-layer composition may, of course, have additional layers to provide utilities specific to other applications. For example, in one application of the moisture detecting materials of the present application, a third material may be employed on either or both sides to prevent sticking to a substrate. This could be useful in an application such as a medical dressing. In one particularly desirable embodiment, a four-layer moisture detecting composition may be prepared having gauze, pigmented netting, gauze, and pigmented nonstick netting adjacent to each other in that order. Where employed in any embodiment, any materials between the pigmented material and a source of liquid should be wicking or otherwise provide for the transport of the liquid to the color indicating material.

Figure 6:
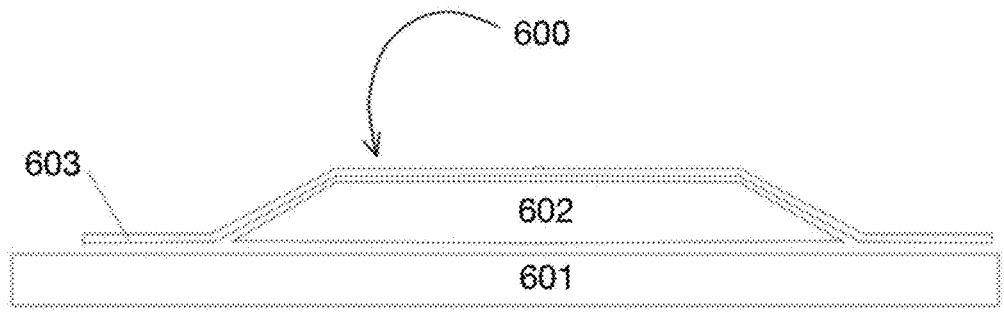
FIG. 6 is an illustration of a moisture detection article comprising a foam having tapered sides used in a dressing.
Figure 7:
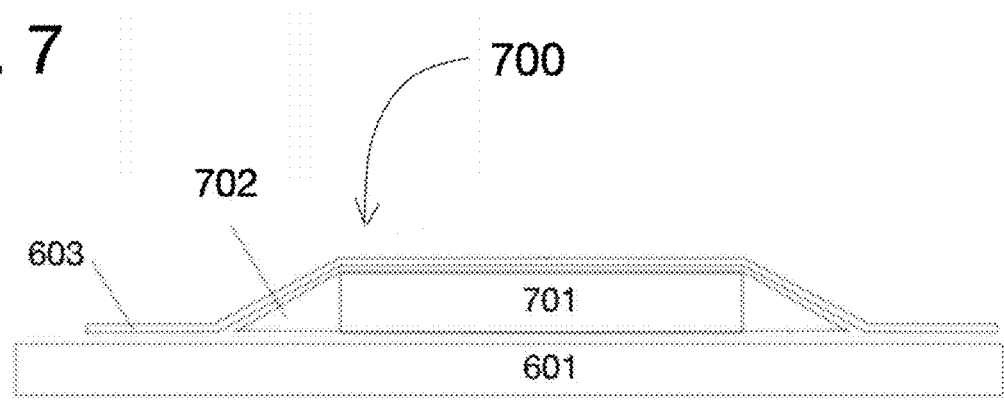
FIG. 7 is an illustration of the prior art foam dressing used to contrast with FIG. 6.

Turning to FIG. 6, a dressing is shown where a foam moisture indicating article (602) is used as part of a dressing (600). The foam is tapered (at about 45 degress) allowing an adhesive film (603) to secure the foam moisture indicating article to skin (601). The amount void area at the junction of the skin, foam, and adhesive layer is thereby minimized. In contrast, a rectangular foam of the prior art is illustrated in FIG. 7. Note that the use of a rectangular foam (701) in a more conventional dressing (700) creates a significant void (702) where the skin (601) is not in contact with the adhesive layer (603). This can reduce the stability of the dressing and the stability can be further reduced if the foam should adsorb enough moisture to swell.

Figure 8:
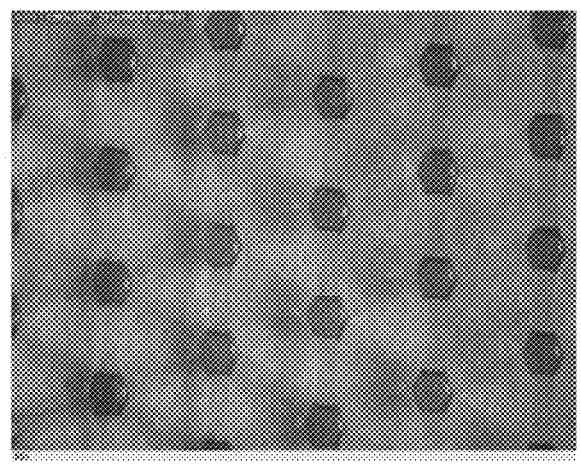
FIG. 8 is an illustration of a photomicrograph of a moisture detection article of the application.

FIG. 8 is an illustration of a photomicrograph of one square inch of a liquid indicating article of the application. It consists of polymer net heat bonded to non-woven cotton producing about 792 small pigmented heat bonded dots having an interconnected web which is essentially massed when dry. When wet, the color both intensifies and spreads over essentially the entire surface.

Figure 9:
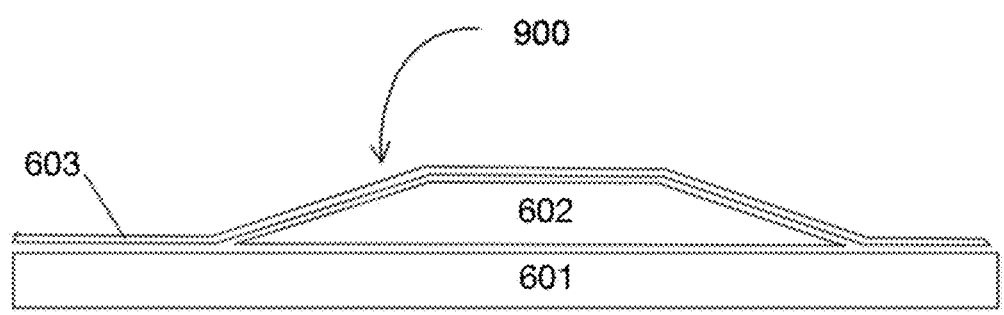
FIG. 9 is an illustration of a dressing similar to that of FIG. 6, except that the foam is more tapered.

FIG. 9 is side view of the dressing (900) of disclosed in FIG. 6 except that the taper is less than about 30 degrees. This is allows for optimization of the use of a liquid indicating article of the application in a dressing where the article comprises a foam.

Figure 10:
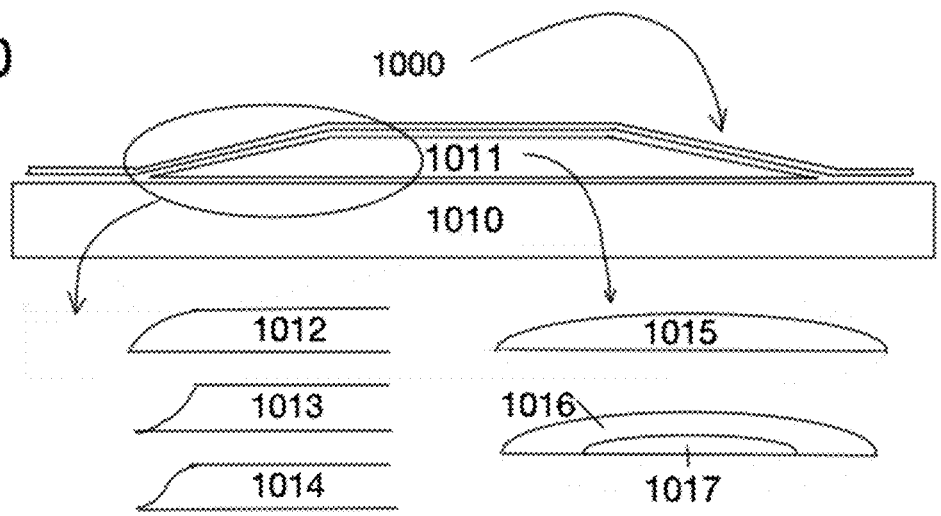
FIG. 10 is an illustration of a foam dressing with alternative features and geometries.

Finally, FIG. 10 is an example of a dressing comprising a foam liquid indicating article (1000) wherein (1011) and (1010) correspond to (602) and (601). Alternative foam taper geometries are illustrated in (1012), (1013) and (1014). Another embodiment of the invention is illustrated in (1015) wherein the foam is curved rather than tapered. Finally, the use of a unitary foam liquid indicator is show where (1017) is a pigmented region within a foam and (1016) is a region that becomes less opaque while in contract with a liquid.

Turning now to Appendix B, displayed is the color photomicrograph which was the basis for FIG. 8. Also show in a photograph of an example of an embodiment of the invention of the application. The original sample is shown on the right and the sample after being wetted with water is shown on the left. This color and appearance change is indicative of a positive indication of the presence of a liquid, in this case water.

EXAMPLE 1

A foam bandage is prepared using the following steps.

An adhesive is deposited on a carrier or release liner (layer 1). This adhesive (layer 2) may be continuous of discontinuous or both in sections or patterns.

The preferred adhesive is a silicone "gel" which attaches well to patients' skin but also releases with minimal pain or trauma. Dow Corning 9700 to 9010 family of SkinSoft® adhesives are typical. Several versions of a low-trauma non-silicone adhesive are also suitable. Often called Hybrid adhesives in the trade. Hot Melt, Hydrocolloid, Polyurethane and Acrylic adhesives are some of the many options. Acrylics and Urethanes are generally a 2-part system requiring highly controlled meter mixing head up application.

Application of the adhesive may be via a computer-controlled 3D printer or X-Y motion with one or several nozzles. Rotogravure or any other deposition technique. The pattern and quantity (thickness) of adhesive may be non-uniform and open areas allowing fluid/air movement are preferred.

The adhesive may be natural or pigmented with a non-leaching pigment such as a dark blue. If a pigmented adhesive is used, more than one color is possible and patterns, words, symbols are also possible.

Gentle heat may be applied to overcome the silicone crosslinking inhibitor and initiate the crosslinking reaction. This step may also be omitted until later. It is important to realize that not all adhesives require this heating step.

On top of the release liner and deposited adhesive is cast a hydrophilic foam layer (layer 3). This layer can be up to 10 mm thick, but 2-4 mm is typical for wound bandages. Thick/thin sections may be created which may also include a tapered perimeter.

The foam may be applied from a roll if it was produced in a prior step or sourced from a vendor. A preferred method is a direct application of components which are mixed and react to generate gas bubbles and create a foam. Multi components are mixes thoroughly, generally, a polyol Part A with an aqueous/surfactant as Part B. A hydrophilic foam results and because it was cast onto the adhesive, it is firmly attached while not inhibiting the adhesive from functioning.

Note, multiple layers of foam are possible. Absorption capacities, softness, color, thickness, additive additions and many other variables are possible. For example, a low-cost roll or commodity foam may be married to a high-performance urethane hydrophilic foam to reduce costs. Superabsorbent granules or antimicrobials may be placed in different layers to impart special features.

Several Polyurethane Prepolymer chemistries are available and useful in foam production. HYPOL family from Dow, AQUAPOL by Carpenter and BAYMEDIX by Covestro are all candidates. Mixing ratios and processing/drying conditions vary. Each can be modified by adjusting the mix to control capacity, density, strength, etc. Additives and colors can be mixed prior to ar at the final mixing head.

Most dressings utilize an occlusive breathable film outer layer to prevent outside contamination from bacteria while allowing airflow for wound health. Polyurethanes, Polyesters and hybrid films with a thickness of 0.0005" to 0.002" are typical. This occlusive layer (layer 4) may be deposited on top of the foam layer (layer 3) while in production. A strong intimate bond results.

By following this general process, complex dressings with adhesive, absorbent foam and occlusive barrier film may be produced in one process.

If a pigmented adhesive or pigmented foam layer is utilized, a wetness indicating structure results. This structure may be modified in numerous ways to produce advanced and high-performance wound dressings economically.

EXAMPLE 2

Spectrometer Test Method

A moisture indicating body of the Application is tested for indicating that it has become wet using the following method. A spectrophotometer having the trade designation DATACOLOR 500 from the DATACOLOR company is employed to do the testing. This type of spectrophotometer is used globally for plastics, paint and textile color measurement. The CIELAB L*a*b* and L*C*h* colorimetric systems are utilized. The method for employing this apparatus is supplied by the vendor and a copy is attached herein as Appendix A.

The test is performed with dry samples which are then wet and measured a second time. The difference between the readings indicates the degree of visual color change.

Lightness, Chroma and Hue determinations are made and reported by the Datacolor 500 Instrument.

A two-layer sample moisture indicating article of the application was prepared and tested using the spectrophotometer. Dry, the sample had an L value of 87.3 and a C Value of 7.68. Wet, the sample had an L value of 70.8 and a C Value of 15.36. The differential values were, respectively, 16.5 and 15.4. Based on the criteria set above, the sample passed the test and it was easy for the human eye to detect the change in appearance when the item became wet.

EXAMPLE 3

Apple App Color Meter Test

Desirably, the moisture detecting articles of the application have a dramatic color change, either in changing from one color to another, or changing in intensity, as possible. For example, in one embodiment, when tested using a smart phone app known as APPLE APP RGB COLOR METER, which is available from the Apple. App Store at the time of filing. This App determines the amount of light in the red green and blue spectrums being reflected off of materials. Something having an absolute black color which by definition would also have no reflectance would have a value of 000 corresponding to the red green and blue colors. Something that reflected essentially all of any of those colors would have a value of 255/255/255. For example, a purely red article would produce a reading of 255/0/0.

Testing was done using an iPhone 6. Samples of the moisture detecting articles of the application had color changes as shown in Table 1:

TABLE 1

| RGB Reflectance of Wet and Dry Materials | | |
|---|---|---|
| Sample ID | Dry Reflectance | Wet Reflectance |
| 1 | 181/178/172 | 132/157/170 |
| 2 | 176/175/177 | 97/135/175 |
| 3 | 150/143/136 | 67/79/90 |
| 4 | 133/136/136 | 77/94/103 |
| 5 | 219/219/224 | 160/182/200 |
| 6 | 204/208/219 | 114/151/191 |
| 7 | 170/165/165 | 81/88/98 |
| 8 | 146/146/144 | 89/92/92 |
| 9 | 207/209/208 | 171/196/211 |
| 10 | 191/192/196 | 127/165/202 |
| 11 | 127/123/119 | 94/100/107 |
| 12 | 113/104/95 | 107/109/109 |

The greater the difference in the numbers for each of the values above, the more apparent that the moisture detecting article was wet. The RGB values will vary according to the color of the materials being used. For example, these numbers are for color changes between white and blue and white and gray. Exemplary of these is sample 5 which was very white when dry and light blue when wet. Sample 7 had a color change of from white to gray. Desirably, the moisture detecting materials of the application will have a change upon getting wet of at least 175 units in at least one of the RGB values. In another embodiment, at least one of the RGB values will change by at least 125 units. In yet another embodiment, at least one of the RGB values will change by at least 100 units. Spectrophotometers are the stand measurement tools for determining textile colors.

What is claimed is:

1. A liquid indicating article comprising:
   a first visible layer having a wet tensile strength of from at least 125 to 350 g/inch that transitions from a first opaque state to a less opaque second state, and
   a second layer having a color different from the less opaque state;
   wherein the visible layer is interlocked to the second layer and the transition of the first layer occurs while in contact with a liquid.

2. The liquid indicating article of claim 1 comprising a woven or nonwoven gauze bonded to a net prepared by perforating a film.

3. The liquid indicting article of claim 1 comprising a woven or nonwoven gauze bonded to a foam.

4. The liquid indicating article of claim 1 wherein the first layer, second layer or both the first layer and the second layer is a non-woven material.

5. The liquid indicating article of claim 1 wherein the second layer is prepared employing pigments that are completely contained within the matrix of the colored layer.

6. The liquid indicating article of claim 5 wherein the pigments are not readily soluble in water and resist transfer to skin upon which it is applied.

7. The liquid indicating article of claim 2 wherein the woven or nonwoven gauze is suitable for use in wound care.

8. The liquid indicating article of claim 3 wherein the woven or nonwoven gauze is suitable for use in wound care.

9. The liquid indicating article of claim 4 wherein both the layers are suitable for use in would care.

10. The liquid indicating article of claim 1 wherein the bonding within the article is water resistant.

11. The liquid indicating article of claim 1 wherein the liquid indicating article has a dry tensile strength of from at least 150 to 400 g/in.

12. The liquid indicating article of claim 1 wherein the liquid indicating article has a wet (isopropanol) tensile strength of from at least 75 to 250 g/in.

13. The liquid indicating article of claim 1 wherein the liquid indicating article has a dry peel strength of from at least 55 to 200 g/in.

14. The liquid indicating article of claim 1 wherein the liquid indicating article has a wet peel strength of from at least 30 to 175 g/in.

15. The liquid indicating article of claim 1 wherein the liquid indicating article has a wet (isopropanol) peel strength of from at least 25 to 150 g/in.

16. The liquid indicating article of claim 1 wherein a layer becoming less opaque while in contact with a liquid has a color or appearance change of at least 10% of the dry L (lightness) or C (chromo) values.

17. The liquid indicating article of claim 1 wherein the layer becoming less opaque while in contact with a liquid has a color or appearance change of at least 20% of the dry L (lightness) or C (chromo) values.

18. The liquid indicating article of claim 17 wherein a layer becoming less opaque while in contact with a liquid has a color or appearance change of at least 30% of the dry L (lightness) or C (chromo) values.

19. The liquid indicating article of claim 1 wherein the liquid indicating article is a dressing.

20. The liquid indicating article of claim 19 wherein the second layer is prepared using pigments that are also additives selected from the group consisting of antibiotics, hemostatics, probiotics and moisturizers, that become active while in contact with a liquid.

21. A process for manufacturing the liquid indicating article of claim 1 comprising applying:
   a first visible layer that transitions from a first opaque state to a less opaque second state, to
   a second layer having a color different from the less opaque state;
   wherein the visible layer is interlocked to the second layer and the transition of the first layer occurs while in contact with a liquid.

22. The process of claim 21 wherein the process is subject to quality assurance by employing a reference grade spectrophotometer to measure color change to the article when the article is contacted with a liquid.

23. The process of claim 22 wherein the layer becoming less opaque while in contact with a liquid has a color or appearance change of at least 10% of the dry L (lightness) or C (chromo) values.

24. The process of claim 21 wherein materials employed in the process are water resistant.

* * * * *